(12) United States Patent
Zhadanov et al.

(10) Patent No.: US 7,934,272 B2
(45) Date of Patent: May 3, 2011

(54) WATER-ACTING DEVICE FOR PERSONAL HYGIENE

(76) Inventors: Sam Zhadanov, Brooklyn, NY (US); Eli Zhadanov, Brooklyn, NY (US)

( * ) Notice: Subject to any disclaimer, the term of this patent is extended or adjusted under 35 U.S.C. 154(b) by 618 days.

(21) Appl. No.: 11/809,442

(22) Filed: Jun. 1, 2007

(65) Prior Publication Data

US 2008/0295243 A1    Dec. 4, 2008

(51) Int. Cl.
*E04H 4/00* (2006.01)
(52) U.S. Cl. .......................................................... 4/448
(58) Field of Classification Search .............. 4/448, 447, 4/443, 420.1, 420.2, 420.4, 420.5; 239/569, 239/576, 586
See application file for complete search history.

(56) References Cited

U.S. PATENT DOCUMENTS

| | | | |
|---|---|---|---|
| 3,758,039 A * | 9/1973 | Wagner | 239/372 |
| 4,286,755 A * | 9/1981 | Shipman | 239/530 |
| 4,371,993 A * | 2/1983 | Patrick | 4/448 |
| 5,197,708 A * | 3/1993 | Campau | 251/8 |
| 6,618,865 B1 * | 9/2003 | Kim | 4/420.4 |

\* cited by examiner

*Primary Examiner* — Huyen Le
(74) *Attorney, Agent, or Firm* — I. Zborovsky

(57) ABSTRACT

A water acting device for personal hygiene has a housing connectable with a water source, a hollow water issuing element connectable with the housing and having an inner passage for passing of water, and means for sealing the water issuing element relative to the housing, the sealing means forming a water passage communicatable with a source of water, and means for adjusting a water supply through the water issuing element, the adjusting means including at least a part of the sealing element and an adjusting member acting on the part of the sealing element so as to change a cross-section of the passage formed by the sealing element, so that the sealing element simultaneously performs functions of sealing of the water issuing element relative to the housing and adjusting or stopping a flow of water through the sealing element to the water issuing element.

5 Claims, 3 Drawing Sheets

US 7,934,272 B2

WATER-ACTING DEVICE FOR PERSONAL HYGIENE

BACKGROUND OF THE INVENTION

The present invention relates to water acting devices for personal hygiene, such as for showering, rinsing, washing, cleaning, spraying, oral care, etc., which operate with the use of water.

More particularly, it relates to the devices of this type which can be attached to water supply systems, for example to a faucet of a water sink, to a shower system in bathrooms and shower rooms, etc. It is believed that the existing devices can be further improved.

SUMMARY OF THE INVENTION

Accordingly, it is an object of the present invention to provide a water acting device for personal hygiene which is a further improvement of the existing devices.

In keeping with these objects and with others which will become apparent hereinafter, one feature of the present invention resides, briefly stated, in water acting device for personal hygiene, comprising a housing connectable with a water source; a hollow water issuing element connectable with said housing and having an inner passage for passing of water; means for sealing said water issuing element relative to said housing, said sealing means forming a water passage communicatable with a source of water; and means for adjusting a water supply through said water issuing element, said adjusting means including at least a part of said sealing element and an adjusting member acting on said part of said sealing element so as to change a cross-section of said passage formed by said sealing element, so that said sealing element simultaneously performs functions of sealing of said water issuing element relative to said housing and adjusting a flow of water through said sealing element to said water issuing element.

When the device is designed in accordance with the present invention, it provides an efficient, concentrated, measured and targeted water stream delivering for personal hygiene.

In accordance with another feature of the present invention a container for preparation of a mixture with an additional substance, liquid or soluble powder, has a spherical inner hollow, so that mixing of the water with the additional substance is provided in a very efficient and thorough way, which increases the quality of mixture and reduces water consumption.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
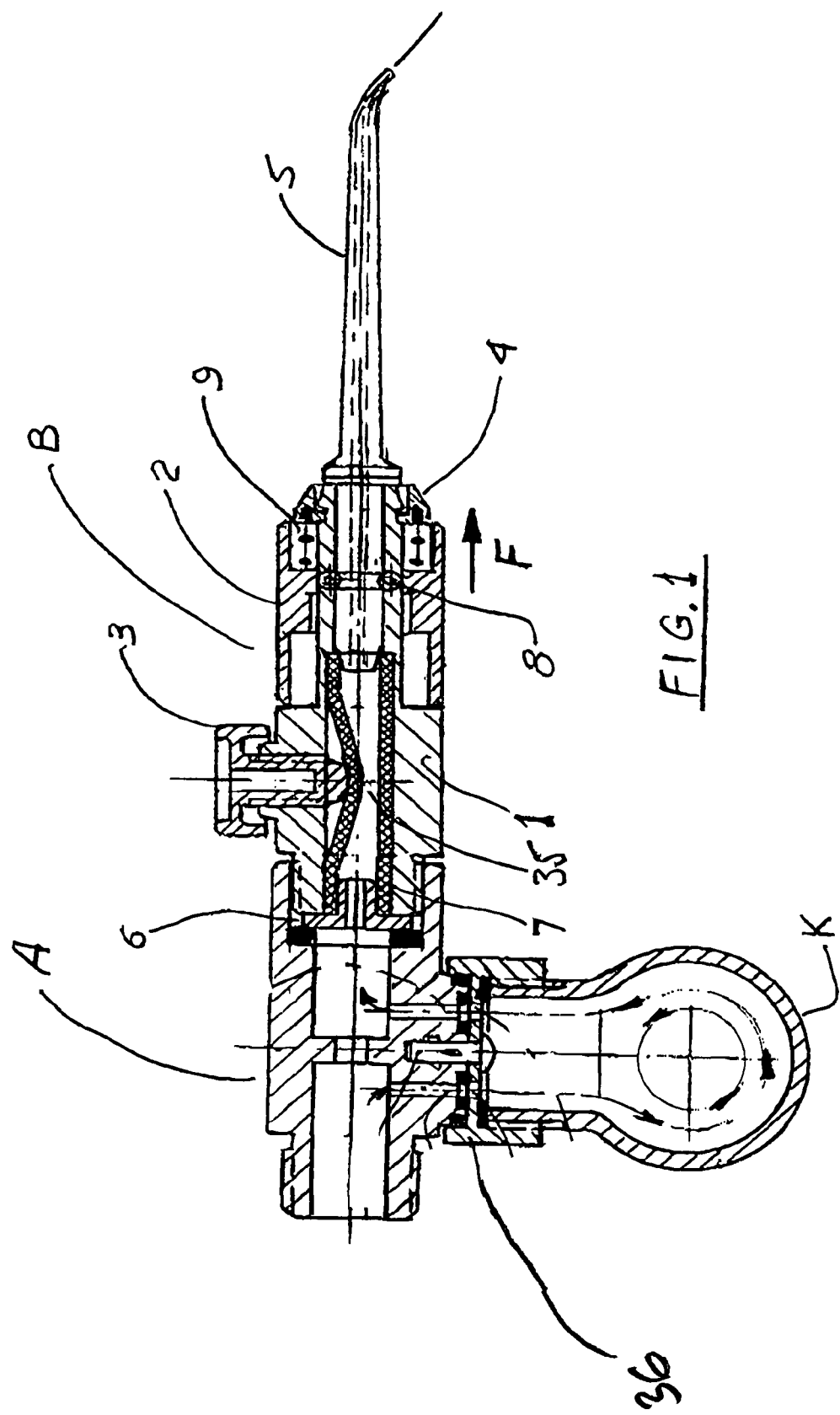
FIG. 1 is view showing a cross-section of a water acting device for personal hygiene in accordance with the present invention.
Figure 2:
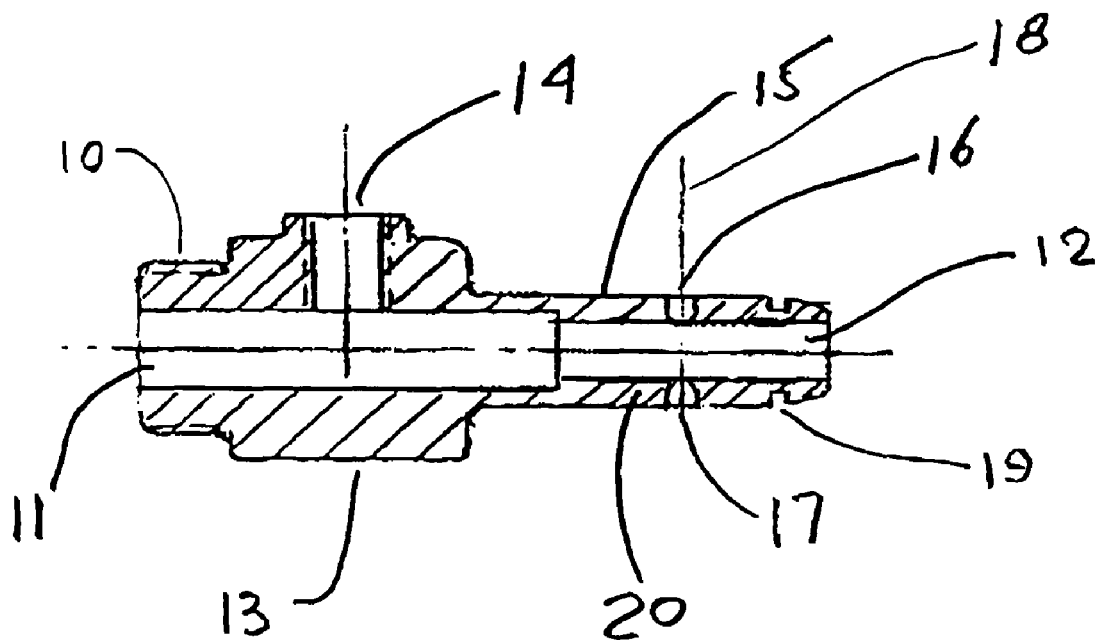
FIG. 2 is a view showing a cross-section of a housing part of the inventive device.
Figure 3:
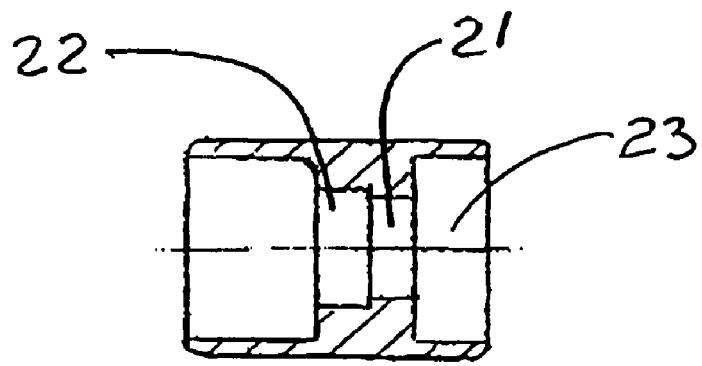
FIG. 3 is a view showing a cross-section of a bushing of the inventive device.
Figure 4:
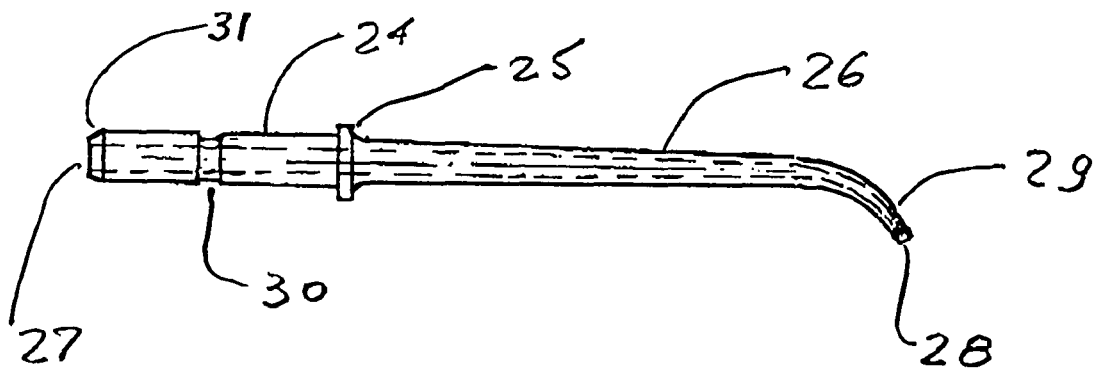
FIG. 4 is a view showing a cross-section of the water issuing element of the inventive device.
Figure 5:
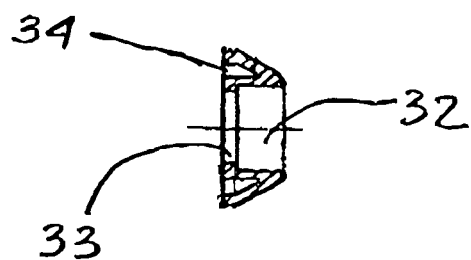
FIG. 5 is a view showing a cross-section of a fixing ring between the bushing and the water issuing element.

A water acting device for personal hygiene in accordance with the present invention has two sections, namely a water mixture preparation section A, and a mechanism of preparation and adjustment of a water jet B.

The mechanism for preparation of a water mixture can be formed, for example, as disclosed in our U.S. Pat. Nos. 5,730, 178 and 5,913,327. Water passes through a container in which liquid or soluble powder additional substance is introduced for mixing with water, and then the mixture is supplied further into the device to be issued for corresponding purposes.

In accordance with the present invention the container K is formed with a spherical inner hollow. In particular it can be formed generally spherical so that both its inner surface and its outer surface are spherical. The important part however is that the inner hollow is spherical. Therefore because of the spherical shape, the mixing of the water passing through the container with an additional substance, liquid or soluble powder, is performed in a very efficient, continuous and uniform way, so that the quantity of the mixture can be introduced and increased.

The valve 36 can be provided to activate or to deactive of the supply of the additional substance from the container (mixing means).

The mechanism for preparation and adjustment of water jet includes a housing which is identified with reference numeral 1. A sealing element 7 is located inside the housing and fixed by a bushing 6. An adjustment member formed as an adjustment screw 3 is screwed in a threaded opening of the housing. A bushing 2 is arranged on the cylindrical part of the housing and a spring 9 is located inside the bushing and abuts against a holding ring 4.

As can be seen from FIG. 1, the screw (7) can be provided with a lower part-spherical surface acting on the sealing element (7).

A water issuing element 5 is arranged in an opening of a cylindrical part of the housing and formed as an elongated jet tip. It is fixed by two balls 8 accommodated in openings of a wall of the cylindrical part of the housing.

The housing 1 has a threaded end 10, cylindrical openings 11 and 12, a cylindrical part 13 with a threaded opening 14, and a cylindrical part 15 with two openings 16 and 17 located on an axis 18, as well as an annular groove 19. The cylindrical part 15 with the inner opening 12 forms a wall 20 with a thickness which is greater than the size of the balls 8 located in the openings 16 and 17.

The bushing 2 has a central opening 21 with a size selected so as to slide on the cylindrical part 15, and an opening 22 which has an increased size for compensation of the size of the balls 8, as well as an opening 23 for the spring.

The water issuing element 5 formed as a jet tip has a cylindrical part 24 with a flange 25, a conical part 26 with an inlet opening 27 and an outlet opening 28 in a bent part 29. The cylindrical part 24 has a groove 30 and a conical end 31. The holding ring 4 has an opening 32 with an annular projection 33 and a depression for the spring 9.

In accordance with the present invention, the sealing element 7 is formed as a tubular element composed of a relatively elastic material, for example of polyurethane, and having an axis extending in a longitudinal direction of the housing 1 and the water issuing element 5. The tubular elastic element 7 forms a passage 35 located upstream of a passage provided inside the water issuing element 5. The right end of the tubular elastic element 7 seals a connection between the water issuing element 5 and the housing 1. The left end of the tubular sealing element 7 provides a sealing between the bushing 6 and the housing 1.

The tubular sealing element 7 forms a part of an adjusting unit together with the screw 3, as well be explained herein below. The tubular elastic element 7 is yieldable in a direction which is transverse to a longitudinal direction, under the action of the adjusting member 3.

The operation of the device is performed in the following manner. The device, in particular the part B is connected to a water supply system directly or through the mechanism for preparation of a water mixture A, by the threaded member 10. Under the action of water pressure, the mixture is supplied through the tubular elastic element 7 and its passage into the water issuing element 5 to the outlet opening 28 so as to form a thin high-pressure jet. This thin high-pressure jet can be used for any water acting treatment purposes for personal hygiene.

By transverse displacement of the adjusting member 3, a transverse cross-section of the inner passage 35 of the tubular sealing element 7 is increased or reduced, so as to reduce or increase a pressure of the jet exiting the outlet 28 of the water issuing element 5.

If it is necessary to replace the water issuing element 5 with the other water issuing element, the bushing 2 is displaced in accordance with arrow F on the cylindrical part 15, so as to release the balls 8 from the groove 30.

It will be understood that each of the elements described above, or two or more together, may also find a useful application in other types of constructions differing from the types described above.

While the invention has been illustrated and described as embodied a water acting device for personal hygiene, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A water acting device for personal hygiene, comprising a housing connectable with a water source and having a cylindrical part; a hollow water issuing element connectable with said housing and having an inner passage for passing of water; and means for sealing said water issuing element relative to said housing, said sealing means forming a water passage communicatable with a source of water, and means for adjusting a water supply through said water issuing element, said adjusting means including at least a part of said sealing element and an adjusting member acting on said part of said sealing element so as to change a cross-section of said passage formed by said sealing element, so that said sealing element simultaneously performs functions of said water issuing element relative to said housing and adjusting a flow of water through said sealing element to said water issuing element, wherein said sealing element is formed a hollow tubular element extending in a longitudinal direction of said housing and said water issuing element and is tightly received in said cylindrical part of said housing, said adjusting member acting on a part of said hollow tubular element transversely to said longitudinal direction and being formed as a screw which is screwed in a threaded opening of said housing and during its screwing acts on the part of said hollow tubular element and changes an inner cross-section of said hollow tubular element, wherein said water issuing element is elongated and has a first end with a tip for issuing water and a second opposite end which is conical and inserted into an opening of said sealing element and further comprising a bushing which surrounds said cylindrical part of said housing, is spring-biased, and has an inner groove, wherein said water issuing element has an outer groove accommodating balls, and wherein said bushing is formed so that when it is displaced by a user against a spring biasing, said balls move out of said outer groove of said water issuing element into said inner groove of said housing, so that the water issuing element can be withdrawn from the housing.

2. A device as defined in claim 1; and further comprising means for mixing water with an additional substance, said mixing means being connected with said housing and locatable between said housing and a source of water so that water passes through said means and is mixed with an additional substance and a mixture is supplied into said housing.

3. A device as defined in claim 2, wherein said mixing means is formed as a container having an inner spherical hollow in which the water is mixed with said additional substance in an efficient manner due a spherical shape of said inner hollow.

4. A device as defined in claim 2; and further comprising a valve element configured to activate or deactivate said mixing means.

5. A device as defined in claim 1, wherein said screw has a part-spherical surface acting on said part of said tubular element.

\* \* \* \* \*